United States Patent
Smale

[11] Patent Number: 6,133,200
[45] Date of Patent: Oct. 17, 2000

[54] HERBICIDAL COMPOSITIONS CONTAINING DMSO

[76] Inventor: Bernard Smale, 2640 SW. Talbot Rd., Portland, Oreg. 97201

[21] Appl. No.: 09/298,862

[22] Filed: Apr. 26, 1999

Related U.S. Application Data

[63] Continuation-in-part of application No. 08/788,243, Jan. 27, 1997, which is a continuation-in-part of application No. 08/475,987, Jun. 7, 1995, Pat. No. 5,597,778, which is a continuation-in-part of application No. 08/300,267, Sep. 2, 1994, abandoned.

[51] Int. Cl.[7] .......................... A01N 25/22; A01N 31/02; A01N 37/10; A01N 43/54; A01N 57/02

[52] U.S. Cl. .......................... 504/206; 504/211; 504/214; 504/323; 504/362

[58] Field of Search .................... 504/116, 206, 504/211, 214, 323, 362

[56] References Cited

U.S. PATENT DOCUMENTS 3,756,801 9/1973 Herschler ...................... 71/65

OTHER PUBLICATIONS

Mussell et al. "Acceleration of bean leaf abscission by [2,4–D] acid applied in [DMSO]". CA 68:21097f, 1968.

Lapham, Virgil T. "The Effectiveness of Some [DMSO]–Herbicide Combinations". Publication of Aquatic Vegetation Control Research, Wildlife and Fisheries Commission, Baton Rouge, LA. p. 438–442, 1996.

Weintraub, Robert L. "DMSO and Plants". Chapter 10 in Dimethyl Sulfoxide, vol. 1. Basic Concepts of DMSO. Stanley W. Jacob et al, eds. NY: Marcel Dekker, Inc. p. 295–315, 1971.

*Primary Examiner*—S. Mark Clardy
*Attorney, Agent, or Firm*—Glenna Hendricks

[57] ABSTRACT

The addition of DMSO to herbicidal compositions makes it possible to decrease the amount of active herbicidal agent required for desired activity without loss of effectiveness against target plants. In some instances, it may be advisable to use up to as 5% DMSO. The addition of the DMSO makes it possible to provide a liquid of relatively high stability.

6 Claims, No Drawings

HERBICIDAL COMPOSITIONS CONTAINING DMSO

APPLICATION FOR PATENT

This application is a continuation-in-part of U.S. Ser. No. 08/788,243, filed Jan. 27, 1997, now pending, which is a continuation-in-part of U.S. Ser. No. 08/475,987 filed Jun. 7, 1995, now U.S. Pat. No. 5,597,778, which is a continuation-in-part of U.S. Ser. No. 08/300,267 filed Sep. 2, 1994, now abandoned.

FIELD OF THE INVENTION

This invention is related to means of enhancing effectiveness of selective herbicides by addition of 1%–2.5% Dimethylsulfoxide (DMSO) to the herbicidal composition whilst reducing the amount of herbicide used. In some instances, especially when the target species has stems or leaves that are particularly impermeable, it may be necessary to increase the amount of DMSO to 3%.

BACKGROUND OF THE INVENTION

The use of herbicides and pesticides has proven to be a mixed blessing to mankind. While the value of increased production of food for human consumption has been important in meeting the nutritional needs of the world, the addition of large amounts of herbicidal substances which are often slowly degraded has caused environmental damage. The regulation of use of herbicides to avoid excess dispersal of these active agents into the environment has become an increasing concern to agriculturalists and environmentalists.

The use of dimethylsulfoxide with herbicides has previously been suggested. A study done in 1964 used DMSO with herbicides in solutions containing 0.5 gpa of DMSO to 1 gpa of a mixture containing picloram-2,4-D mixture. Using this large amount of DMSO proved to result in efficacious killing of plants. However, the use of such large amounts of DMSO (33%) in herbicidal compositions has not been practiced, and would undoubtedly be too expensive for widespread use. Furthermore, as indicated in this specification, such concentrations are neither necessary nor advisable.

DMSO has also been used in insecticidal compositions. U.S. Pat. No. 3,321,364 discloses use of DMSO with the insecticide for use in compositions containing ryania. The DMSO is in very small amount and appears to be used primarily as a solubilizing agent.

Keil, of the U.S. Department of Agriculture has suggested use of bacteriocidal and fungicidal compositions containing oxytetracycline and 0.25% to 0.5% DMSO. No use of DMSO in herbicidal compositions is taught therein. Keil suggested that the increased effectiveness was apparently due to the increased absorption and translocation of the active agents.

Robert L. Weintraub has studied the effect of DMSO on plants. He found that aqueous solutions containing 40% or greater amounts of DMSO on cacao seedling caused marginal necroses. It was reported that addition of 0.05% to 15% DMSO to various nutritional supplements such as salts, nutrients, metabolites and dyes resulted in increased absorption.

It has also been reported that use of 10% to 100% DMSO as a solvent enhanced penetration of herbicide to leaves. It goes without saying that use of 10% to 100% DMSO would be prohibitively expensive for use in agricultural application.

It was also reported that use of 1% to 5% DMSO in fungicidal compositions resulted in enhancement of action of some fungicides. No improvement in effect was seen when used with some of the fungicides.

DESCRIPTION OF THE INVENTION

It is the purpose of this invention to provide improved post-emergent herbicidal compositions containing greatly reduced amounts of herbicide in formulations containing 0.5 to 2.5% of DMSO. When the target species is particularly impermeable to herbicidal agents, the amount of DMSO in the herbicidal composition may be as high as 3%. A preferred range for DMSO concentration is 1% to 2% DMSO. At the levels of DMSO taught herein, it is possible to avoid damage to the plant absorption process whilst greatly decreasing the amount of herbicide necessary to obtain highly effective selective response.

The method of the invention may often be practiced by preparing a concentrated composition comprising an herbicide and anhydrous dimethylsulfoxide. Various additives, including detergents, emulsifiers and dispersing agents may be added along with an agriculturally acceptable carrier to provide the desired concentration of active agent for application to plants. In a preferred embodiment, the method of preparation of the composition for application comprises the steps of 1) solubilizing a dry herbicidal composition in anhydrous dimethylsulfoxide, 2) adding additional dimethylsulfoxide and a surfactant to the composition prepared in step 1, and then 3) adding to the composition prepared in step 1 sufficient agriculturally acceptable carrier to provide a composition containing final composition of 1% to 3% dimethylsulfoxide and a selectively herbicidal amount of a post-emergent herbicide. Anhydrous surfactant may be added to the composition along with the anhydrous dimethylsulfoxide.

In many instances, it may be particularly important to use either the anhydrous or reagent grade DMSO rather than commercial grade DMSO, since contaminants in the aqueous phase may interfere with full activity of the products.

Because DMSO is readily degraded in the natural environment, the addition of DMSO does not present a lingering danger to the ecosystem. The enhancement of the herbicidal activity occasioned by use of DMSO in concentrations taught herein makes it possible to greatly decrease the amount of herbicide that could have more lingering effects when released into the environment. The methods using the preferred amounts disclosed herein will also result in financial savings.

Finally, it is possible to obtain short-term herbicidal effects while decreasing the term of residual soil activity. This reduction is particularly important when using agents such as sulfonylurea herbicides. Most crops planted in fields previously treated with these herbicides are subject to injury if residual soil activity remains after treatment with these herbicides. The rotational intervals for the sulfonyl ureas range from 3–15 months, and may be even longer when the herbicide is applied over other herbicides. The major factors contributing to the soil activity are herbicide use rate, soil pH, moisture, and air and soil temperature. Of these, only the use rate can be readily modified in the field. However, lowering the use rate may limit effectiveness at all time periods following application. By adding DMSO to the carrier as taught herein, it is possible to retain short-term efficacy while lowering the use rate, thus shortening the rotational cycle without loss of short-term efficacy.

It was found that use of about 1% DMSO most frequently resulted in minimal loss of the preferred species of plants while minimizing the amount of active herbicide needed to obtain desired results against the weed population. Use of up to 3% DMSO is acceptable and provides improved effectiveness in a few instances. However, when more that 3% DMSO was present in the compositions, the young crop plants were more likely to be damaged. Moreover, unnecessary cost was incurred by the addition of unnecessarily high levels of DMSO without any increase in benefit. By methods of the invention it has been possible to decrease amount of herbicide in the compositions by 25% to 75% without loss of short term herbicidal activity.

EXAMPLE 1

Phytotoxicity of DMSO sprays was evaluated on hosta, ferns and azaleas. In each instance, groups of 6 plants were sprayed with 1%, 2%, 5% or 10% aqueous DMSO.

TABLE 1

| Plants | Concentration DMSO | Effects |
|--------|-------------------|---------|
| hosta  | 10%               | Margina burn |
| ferns  | 10%               | burn on fron tips |
| azalea | 10%               | non-toxic |
| hosta  | 5%                | non-toxic |
| ferns  | 5%                | burn on fron tips |
| azalea | 5%                | non-toxic |
| hosta  | 2%                | non-toxic |
| ferns  | 2%                | non-toxic |
| azalea | 2%                | non-toxic |

At 1% DMSO on all tests, no toxicity was noted.

EXAMPLE 2

A commercial product containing as active agents 2,4 dichlorophenoxy acetic acid and 2-(2-methyl-4-chlorophenoxy) propionic acid (Composition A) was evaluated. The recommended rate of application is 4 teaspoons per gallon. Lower rates of 1 and 2 teaspoons per gallon with DMSO added to provide DMSO concentration of 1%, 0.5% and 0.25% were tested. All plants were sprayed to thoroughly wet the leaves with the following results:

TABLE 2

| Conc. Comp. A | Conc. DMSO | Plantain | Thistle | Ground Ivy | Curly dock |
|---------------|------------|----------|---------|------------|------------|
| 4 tsp/gal | 0 | ++ | ++ | ++ | ++ |
| 2 tsp/gal | 0 | + | ± | ± | ± |
| 1 tsp/gal | 0 | -- | -- | -- | -- |
| 4 tsp/gal | 1% | ++++ | ++++ | ++++ | ++++ |
| 2 tsp/gal | 1% | ++++ | ++++ | ++++ | ++++ |
| 1 tsp/gal | 1% | ++ | ++ | ++ | ++ |

Definitions:
-- = no effect on plants
+ = slight effect
± = slight to no effect
+++ = moderate effect
**** = severe damage to plant Retesting showed similar effects with more DMSO.

EXAMPLE 3

Glyphosate (N-(phosphonomethyl)glycine), the active agent (41%) in Composition B and other similar non-selective herbicidal products for control of many annual and perennial grasses, broadleaf weeds, woody shrubs and trees was evaluated in greenhouse studies. The $LD_{50}$ range for glyphosate in the commercial concentrate Composition B on sickle pod grown in the greenhouse was established at 0.06%, and 0.03%. Comparisons of percent control of sickle pod by glyphosate with and without DMSO (3%) showed significant improvement in sickle pod control at 0.06% and 0.03% when 3% DMSO was present over control when DMSO was lacking.

Evaluation of effect of the 0.06% glyphosate concentrate over a 30 day interval clearly demonstrated improved early and sustained control of sickle pod with compositions containing 3% DMSO. Data showing effectiveness for control of sickle pod at concentration 0.06% and 0.3% in carrier with 3% DMSO are shown below. The testing procedure used 12 sickle pod 3 inches high selected for uniformity in each treatment. The rating of injury to each plant was based on visual rating of herbicidal activity with +=10%, ++=25%, +++=50%, ++++−75% and dead plants=100%.

| % herbicide and additive | % control of sickle pod at 12 days |
|--------------------------|------------------------------------|
| 0.06% glyphosate only | 51% |
| 0.06% glyphosate with 3% DMSO | 90% |
| 0.03% glyphosate only | 54% |
| 0.03% glyphosate with 3% DMSO | 85% |

Evaluation of the 0.06% glyphosate concentration over a 30 day interval clearly established improved early and sustained control of sickle pod with 3% DMSO compared with control using the glyphosate only.

|  | 12 days | 20 days | 30 days |
|--|---------|---------|---------|
| 0.06% glyphosate only | 51% | 43% | 85% |
| 0.06% glyphosate, 3% DMSO | 90% | 85% | 96% |

EXAMPLE 4

Two sulfonyl urea herbicides were tested. A 75% by weight of (((((4,6-dimethoxypyrimidin-2-yl) aminocarbonyl))aminosulfonyl))-N,N-dimethyl-3-pyridinecarboxamide (Composition C) and a composition containing as an active agent 25% ethyl 2-[[[[(4-chloro-6-methoxy-2-pyrimidin-2-yl)-amino]carbonyl]amino] sulfonyl]benzoate, also known as chlorimuron ethyl, (Composition D) which provide selective weed control of may grasses and broad leaf weeds in crops such as peanuts, alfalfa, soybean, rice, cereal grains and cotton, were tested. Use rates of sulfonyl urea herbicides such as Composition C and Composition D are low, ranging from ¼ to 1½ ounces per acre.

Green house experiments were conducted demonstrating the sustained efficacy of Composition C and Composition D at one-half the rate suggested on the label. Composition C label directions for control of annual morning glory (2–3 inches height) call for use of ⅔ ounces per acre. Composition D labels stipulates the same amount for control of annual morning glory and sickle pod. Data show no loss of effectiveness with these active agents when the rate of application was reduced to ⅓ ounce per acre. Increased herbicidal activity with Composition C plus DMSO at 0.66 ounces per acre and 0.33 ounces per acre applications was shown.

| Product and concentration | 9 days | 21 days |
|---|---|---|
| | % control, morning glory | |
| C at 0.66 oz/A | 33% | 52% |
| C at 0.66 oz/A, 2% DMSO | 52% | 67% |
| C at 0.33 oz/A, 2% DMSO | 55% | 65% |
| | % control, sickle pod | |
| D at 0.66 oz/A | 57.5% | 85% |
| D at 0.66 oz/A, 2% DMSO | 77.5% | 95% |
| D at 0.33 oz/A, 2% DMSO | 75% | 90% |
| | % control, morning glory | |
| D at 0.66 oz/A | 75% | 75% |
| D at 0.66 oz/A, 2% DMSO | 82.5% | 80% |
| D at 0.33 oz/A, 2% DMSO | 85% | 92.5% |

Compositions of selective and nonselective post emergence herbicides are prepared using 25% to 75% of the recommended amount of the following in carrier containing 1%–2.5% DMSO carrier are prepared in the same manner using other herbicides including atrazine (6-chloro-N-ethyl-N'-(1-methylethyl)1,3,5-triazine-2,4-diamine), chlorsulfuron (2-chloro-N-[[(4-methoxy-6-methyl-1,3,5-triazin-2-yl)-amino]carbonyl]benzenesulfonamide), linuron(N'-(3,4-dichlorophenyl)-N-methoxy-N-methylurea), chlorimuronethyl(ethyl2-[[[[(4-chloro-6-methoxypyrimidin-2-yl)-amino]-carbonyl]amino]sulfonyl]benzoate), dalapon(2,2-dichloro-propanic acid), MCPA(4-chloro-2-methylphenoxyacetic acid), diquat(6,7-dihydrodipyrido[1,2-a:2',1'-c]pyrazinediiumdibromide), 2,4D(2,4dichlorophenoxyacetic acid), propanil(N-(3,4-dichloropheny)propanamide), alachlor(2-chloro-N-(2,6-diethylphenyl-N-methoxymethyl)-acetamide), fluometuron (N,N-dimethyl-N'-[3-(trifluoro-methyl)pheny]urea), chloramben(3-amino-2,5-dichloro-benzoic acid), fluazifopbutyl(2-[4-[[5-(trifluoro-methyl)-2-pyridinyl]oxy] phyenoxy]propanoic acid butylester), amitrole(1H-1,2,4-triazol-3-amine), bentazon (3-(1-methylethyl)-1H-2,1,3-benzothadiazin-4(3H)-one 2,2 dioxide), paraquat(1,1'-diemthyl-4,4'-bipyridinium), diclofopmethyl(2-[4-(2,4-dochlorophenoxy-)-phenoxy]propanoic acid methyl ester), terbutryn, tebuthiuron (1-(5-tert-butyl-1,3,4-thiadiazol-2-yl)-1,3-diemthyl-urea), thiobencarb, sethoxydim (2-[1-ethoxyimino)butyl]-5-[2-(ethoxythio)propyl]-3-hydroxy-2-cyclohexen-1-one), dicamba (3,6-dichloro-2-methoxybenzoic acid), pendi-methalin (N--(1-ethylpropyl)-3,4-dimethyl-2,6-dinitro-benzenamine), and so forth useful for practice of the invention.

EXAMPLE 5

While smaller amounts of DMSO are useful, glyphosate is most effective when the DMSO content is 2.5% to 3% of the final composition. Based on $LD_{50}$ herbicidal activity range for glyphosate on sickle pod under 6 inches tall, field sprays for control should be prepared as follows: Mix 2.4 quarts anhydrous DMSO, 2 pints a concentrate containing 41% glyphosate and 1.5 pints of a commercial surfactant containing oxylated octal phenol prepared by reacting isooctylphenol with ethylene oxide was added to 14 gallons of water in a spray tank with agitator running. Concentrations of DMSO+the surfactant in finished spray will be 3% and 2% respectively, and concentration of glyphosate will be ½ the recommended rate for 3 inch sickle pod (0.625%). The 20 gallon finish spray is sufficient for one acre.

EXAMPLE 6

Composition C, 0.33 oz (½ the label rate for control of 1–3 inch morning glory) is dissolved in 1 quart of anhydrous DMSO. An additional 1¾ gallons anhydrous DMSO is added with mixing. The DMSO/Composition C concentrate is added to 1 quart of the surfactant, which is then added to 100 gallons of water in a spray tank with agitator running is then applied to 1 acre. Concentration in the final product of surfactant and DMSO in finished spray are 0.25% and 2% respectively.

EXAMPLE 7

0.66 oz Composition D (½ the label rate for control of 1–3 inch morning glory) is dissolved in 1 quart of anhydrous DMSO. An additional 1¾ gallons anhydrous DMSO is added with mixing. The DMSO/Composition D concentrate and 1 quart of surfactant are added to 100 gallons of water in a spray tank with agitator running and is then applied to 1 acre. Concentration in the final product of surfactant and DMSO in finished spray are 0.25% and 2% respectively.

EXAMPLE 8

Compositions using glyphosate as formulated for application in the garden were compared with compositions containing ½ strength glyphostate with sufficient DMSO and water added to provide 3% DMSO in the finish spray as applied were compared. The area in which blackberry vines were sprayed with the standard commercial spray containing glyphosate showed significant regrowth of blackberry vines next year after the application. The area in which blackberry vines were sprayed with ½ commercial strength glyphosate in a spray containing 3% DMSO has shown no noticeable regrowth of blackberry vines after a period of 4 years.

In a second comparison using the standard commercial glyphosate spray sold to gardeners and glyphostate diluted with water and DMSO to attain a final concentration of ½ strength glyphostate found in the commercial preparation and 3% DMSO were sprayed on bamboo. The next spring, the area sprayed with the commercial product had small shoots of bamboo growing in the area. The area sprayed with the composition containing 3% DMSO with glyphosate at ½ the concentration found in the commercial preparation showed no growth of bamboo shoots.

An added advantage provided by use of DMSO in formulations is that the liquid formulations are more stable than other liquid formulations. At the present time, many herbicides must be formulated from dry products close to the time for application. The concentrates containing DMSO and herbicide showed no change of pH or lowering of activity when tested after two months. The ability to formulate the herbicidal compositions by solubilizing with DMSO for later use eases the preparation of the final composition for use near the site of use. Hence, the method of formulation using DMSO taught herein provides a means of producing liquid compositions having increased stability.

While the greatest percentage of improvement is seen at concentrations of ≦3% DMSO and, it most instances, the addition of a greater amount of DMSO provides little improvement in efficacy, it has been found that some herbicidal agents are enhanced by use of DMSO at up to 5% concentration of DMSO, especially on woody plants or plants which are very mature. It is suggested that the determination of concentration of DMSO in the applied herbicidal composition requires a balancing of the cost of DMSO and the amount of increased efficacy obtained from the herbicide as measured by the amount of decrease in active herbicidal agent that is obtained using the addition of DMSO.

In making the dilute compositions for administration to the plants, various detergents, emulsifiers and dispersing agents are used. Use of α-[4-(1,1,3,3,-tetramethylbutyl) phenyl]-hydroxypoly(oxy-1,2,ethyanediyl also known as octoxynol is exemplified. However, other emulsifiers, detergents and dispersing agents known in the art can be used in accord with the teachings of the art.

It may also be appropriate to add other pesticides, including insecticides and fungicides, to the compositions of the invention. To prevent hydrolyzation the herbicide in DMSO alone or with other components, but lacking water, may be formulated and shipped for hydration immediately before application. To prevent freezing, agents such as glycol may be added to the concentrated formulations. The concentrates containing DMSO may be placed in containers for shipping. For example strong, impervious bags of that may be opened and emptied into the mixer for dilution may be used for shipment.

What we claim is:

1. A composition of matter comprising at least one post-emergent herbicide, an agriculturally acceptable carrier and dimethyl sulfoxide wherein the dimethyl sulfoxide accounts for from 3% up to and including 5% of the total volume of said composition and the post-emergent herbicide is present at a concentration of from 25% to 75% less than the commercially recommended concentration of herbicide in the spray formulation without DMSO.

2. A composition of claim 1 containing a sulfonylurea.

3. A composition of claim 2 containing chlorimurion ethyl.

4. A composition of claim 1 containing 2,4-dichlorophenoxy acetic acid.

5. A composition of claim 1 containing 2-(4-chloro-2-methylphenoxy)propionic acid.

6. A composition of claim 1 containing glyphosate.

* * * * *